(12) United States Patent
Sanders et al.

(10) Patent No.: US 9,833,605 B2
(45) Date of Patent: Dec. 5, 2017

(54) FLUID TRANSFER DEVICE AND PACKAGING THEREFOR

(71) Applicant: Becton Dickinson and Company Limited, Dun Laoghaire (IE)

(72) Inventors: Laurie Sanders, Glen Ridge, NJ (US); Jayeon Kim, Little Ferry, NJ (US)

(73) Assignee: Becton Dickinson and Company Limited, Dun Laoghaire (IE)

( * ) Notice: Subject to any disclaimer, the term of this patent is extended or adjusted under 35 U.S.C. 154(b) by 127 days.

(21) Appl. No.: 14/691,952

(22) Filed: Apr. 21, 2015

(65) Prior Publication Data

US 2015/0297881 A1 Oct. 22, 2015

Related U.S. Application Data

(60) Provisional application No. 61/982,049, filed on Apr. 21, 2014, provisional application No. 61/982,091, filed on Apr. 21, 2014, provisional application No. 62/050,930, filed on Sep. 16, 2014.

(51) Int. Cl.
 *A61M 39/10* (2006.01)
 *A61J 1/20* (2006.01)

(52) U.S. Cl.
 CPC ........ *A61M 39/1011* (2013.01); *A61J 1/2055* (2015.05); *A61J 1/2096* (2013.01); *A61M 2039/1066* (2013.01)

(58) Field of Classification Search
 CPC ...... A61M 2039/1066; A61M 39/1011; A61M 39/10; A61M 39/1055; A61M 2039/1077; A61M 2039/1083; A61M 2039/1088; A61J 1/2055; A61J 1/2096
 See application file for complete search history.

(56) References Cited

U.S. PATENT DOCUMENTS

| 4,436,125 A | 3/1984 | Blenkush |
| 4,564,054 A | 1/1986 | Gustavsson |
| 4,673,404 A | 6/1987 | Gustavsson |
| 4,932,937 A | 6/1990 | Gustavsson et al. |

(Continued)

FOREIGN PATENT DOCUMENTS

| EP | 2462971 A1 | 6/2012 |
| WO | 0128490 A1 | 4/2001 |

(Continued)

*Primary Examiner* — Quynh-Nhu H Vu
(74) *Attorney, Agent, or Firm* — The Webb Law Firm

(57) ABSTRACT

A fluid transfer system includes packaging having a body with a sidewall extending between an open top end and a bottom end and defining an interior cavity, and at least one protrusion extending radially inward from the sidewall into the interior cavity. The system also includes a fluid transfer device including an inner member and an outer member surrounding at least a portion of the inner member. The inner member having a first position where the inner member is configured to rotate freely relative to the outer member and a second position where rotation of the inner member relative to the outer member is restricted in a first rotational direction. The fluid transfer device also including a locking arrangement configured for cooperating with the at least one protrusion to prevent rotation of the inner member relative to the outer member upon an application of a compressive force on the packaging.

17 Claims, 18 Drawing Sheets

(56) References Cited

U.S. PATENT DOCUMENTS

| | | |
|---|---|---|
| 5,052,725 A | 10/1991 | Meyer et al. |
| 5,104,158 A | 4/1992 | Meyer et al. |
| 5,122,129 A | 6/1992 | Olson et al. |
| 5,280,876 A | 1/1994 | Atkins |
| 5,290,254 A | 3/1994 | Vaillancourt |
| 5,322,518 A | 6/1994 | Schneider et al. |
| 5,334,188 A | 8/1994 | Inoue et al. |
| 5,360,011 A | 11/1994 | McCallister |
| 5,395,348 A | 3/1995 | Ryan |
| 5,437,650 A | 8/1995 | Larkin et al. |
| 5,464,123 A | 11/1995 | Scarrow |
| 5,472,430 A | 12/1995 | Vaillancourt et al. |
| 5,478,328 A | 12/1995 | Silverman et al. |
| 5,487,728 A | 1/1996 | Vaillancourt |
| 5,507,733 A | 4/1996 | Larkin et al. |
| 5,509,911 A | 4/1996 | Cottone, Sr. et al. |
| 5,545,152 A | 8/1996 | Funderburk et al. |
| 5,607,392 A | 3/1997 | Kanner |
| 5,609,584 A | 3/1997 | Gettig et al. |
| 5,611,792 A | 3/1997 | Gustafsson |
| 5,647,845 A | 7/1997 | Haber et al. |
| 5,685,866 A | 11/1997 | Lopez |
| 5,807,347 A | 9/1998 | Bonaldo |
| 5,897,526 A | 4/1999 | Vaillancourt |
| 6,063,068 A | 5/2000 | Fowles et al. |
| 6,089,541 A | 7/2000 | Weinheimer et al. |
| 6,113,583 A | 9/2000 | Fowles et al. |
| 6,132,404 A | 10/2000 | Lopez |
| 6,139,534 A | 10/2000 | Niedospial, Jr. et al. |
| 6,221,041 B1 | 4/2001 | Russo |
| 6,221,056 B1 | 4/2001 | Silverman |
| 6,343,629 B1 | 2/2002 | Wessman et al. |
| 6,358,236 B1 | 3/2002 | DeFoggi et al. |
| 6,378,714 B1 | 4/2002 | Jansen et al. |
| 6,409,708 B1 | 6/2002 | Wessman |
| 6,474,375 B2 | 11/2002 | Spero et al. |
| 6,478,788 B1 | 11/2002 | Aneas |
| 6,544,246 B1 | 4/2003 | Niedospial, Jr. |
| 6,551,299 B2 | 4/2003 | Miyoshi et al. |
| 6,585,695 B1 | 7/2003 | Adair et al. |
| 6,599,273 B1 | 7/2003 | Lopez |
| 6,610,040 B1 | 8/2003 | Fowles et al. |
| 6,629,958 B1 | 10/2003 | Spinello |
| 6,656,433 B2 | 12/2003 | Sasso |
| 6,715,520 B2 | 4/2004 | Andreasson et al. |
| 6,814,726 B1 | 11/2004 | Lauer |
| 6,852,103 B2 | 2/2005 | Fowles et al. |
| 6,875,203 B1 | 4/2005 | Fowles et al. |
| 6,875,205 B2 | 4/2005 | Leinsing |
| 6,911,025 B2 | 6/2005 | Miyahara |
| 6,997,917 B2 | 2/2006 | Niedospial, Jr. et al. |
| 7,040,598 B2 | 5/2006 | Raybuck |
| 7,083,605 B2 | 8/2006 | Miyahara |
| 7,097,209 B2 | 8/2006 | Unger et al. |
| 7,261,707 B2 | 8/2007 | Frezza et al. |
| 7,306,584 B2 | 12/2007 | Wessman et al. |
| 7,326,194 B2 | 2/2008 | Zinger et al. |
| 7,350,535 B2 | 4/2008 | Liepold et al. |
| 7,354,427 B2 | 4/2008 | Fangrow |
| 7,452,349 B2 | 11/2008 | Miyahara |
| 7,547,300 B2 | 6/2009 | Fangrow |
| 7,628,772 B2 | 12/2009 | McConnell et al. |
| 7,648,491 B2 | 1/2010 | Rogers |
| 7,658,734 B2 | 2/2010 | Adair et al. |
| 7,743,799 B2 | 6/2010 | Mosler et al. |
| 7,744,581 B2 | 6/2010 | Wallen et al. |
| 7,758,560 B2 | 7/2010 | Connell et al. |
| 7,803,140 B2 | 9/2010 | Fangrow, Jr. |
| 7,857,805 B2 | 12/2010 | Raines |
| 7,867,215 B2 | 1/2011 | Akerlund et al. |
| 7,879,018 B2 | 2/2011 | Zinger et al. |
| 7,900,659 B2 | 3/2011 | Whitley et al. |
| 7,927,316 B2 | 4/2011 | Proulx et al. |
| 7,942,860 B2 | 5/2011 | Horppu |
| 7,975,733 B2 | 7/2011 | Horppu et al. |
| 8,096,525 B2 | 1/2012 | Ryan |
| 8,122,923 B2 | 2/2012 | Kraus et al. |
| 8,123,738 B2 | 2/2012 | Vaillancourt |
| 8,137,332 B2 | 3/2012 | Pipelka |
| 8,167,863 B2 | 5/2012 | Yow |
| 8,177,768 B2 | 5/2012 | Leinsing |
| 8,196,614 B2 | 6/2012 | Kriheli |
| 8,206,367 B2 | 6/2012 | Warren et al. |
| 8,211,069 B2 | 7/2012 | Fangrow, Jr. |
| 8,225,826 B2 | 7/2012 | Horppu et al. |
| 8,226,628 B2 | 7/2012 | Muramatsu et al. |
| 8,257,286 B2 | 9/2012 | Meyer et al. |
| 8,267,127 B2 | 9/2012 | Kriheli |
| 8,277,424 B2 | 10/2012 | Pan |
| 8,317,741 B2 | 11/2012 | Kraushaar |
| 8,317,743 B2 | 11/2012 | Denenburg |
| 8,398,607 B2 | 3/2013 | Fangrow, Jr. |
| 8,403,905 B2 | 3/2013 | Yow |
| 8,425,487 B2 | 4/2013 | Beiriger et al. |
| 8,449,521 B2 | 5/2013 | Thorne, Jr. et al. |
| 8,454,579 B2 | 6/2013 | Fangrow, Jr. |
| 2003/0070726 A1 | 4/2003 | Andreasson et al. |
| 2005/0065495 A1 | 3/2005 | Zambaux |
| 2005/0182383 A1 | 8/2005 | Wallen |
| 2005/0215976 A1 | 9/2005 | Wallen |
| 2006/0178638 A1 | 8/2006 | Reynolds |
| 2007/0079894 A1 | 4/2007 | Kraus et al. |
| 2008/0045919 A1 | 2/2008 | Jakob et al. |
| 2008/0287914 A1 | 11/2008 | Wyatt et al. |
| 2009/0159485 A1 | 6/2009 | Jakob et al. |
| 2010/0168638 A1 | 7/2010 | Korogi et al. |
| 2010/0179506 A1 | 7/2010 | Shemesh et al. |
| 2010/0217226 A1 | 8/2010 | Shemesh |
| 2011/0004183 A1 | 1/2011 | Carrez et al. |
| 2011/0062703 A1 | 3/2011 | Lopez et al. |
| 2011/0074148 A1 | 3/2011 | Imai |
| 2011/0106046 A1 | 5/2011 | Hiranuma et al. |
| 2011/0257621 A1 | 10/2011 | Fangrow |
| 2011/0291406 A1 | 12/2011 | Kraft et al. |
| 2012/0035580 A1 | 2/2012 | Fangrow |
| 2012/0046636 A1 | 2/2012 | Kriheli |
| 2012/0123381 A1 | 5/2012 | Kraus et al. |
| 2012/0192968 A1 | 8/2012 | Bonnal et al. |
| 2012/0192976 A1 | 8/2012 | Rahimy et al. |
| 2012/0203193 A1 | 8/2012 | Rogers |
| 2012/0265163 A1 | 10/2012 | Cheng et al. |
| 2012/0279884 A1 | 11/2012 | Tennican et al. |
| 2012/0316536 A1 | 12/2012 | Carrez et al. |
| 2013/0006211 A1 | 1/2013 | Takemoto |
| 2013/0012908 A1 | 1/2013 | Yeung |
| 2013/0066293 A1* | 3/2013 | Garfield ............... A61J 1/10 604/408 |
| 2013/0072893 A1 | 3/2013 | Takemoto |
| 2013/0076019 A1 | 3/2013 | Takemoto |
| 2013/0079744 A1 | 3/2013 | Okiyama et al. |

FOREIGN PATENT DOCUMENTS

| | | |
|---|---|---|
| WO | 2005011781 A1 | 2/2005 |
| WO | 2006058435 A2 | 6/2006 |
| WO | 2006103074 A1 | 10/2006 |
| WO | 2009024807 A1 | 2/2009 |
| WO | 2009090627 A1 | 7/2009 |
| WO | 2011050333 A1 | 4/2011 |
| WO | 2011150037 A1 | 12/2011 |
| WO | 2012069401 A1 | 5/2012 |
| WO | 2012119225 A1 | 9/2012 |
| WO | 2012168235 A1 | 12/2012 |
| WO | 2013025946 A1 | 2/2013 |
| WO | 2013054323 A1 | 4/2013 |
| WO | 2013066779 A1 | 5/2013 |
| WO | 2013115730 A1 | 8/2013 |
| WO | 2013179596 A1 | 12/2013 |
| WO | 2014122643 A1 | 8/2014 |
| WO | 2014181320 A1 | 11/2014 |

* cited by examiner

FLUID TRANSFER DEVICE AND PACKAGING THEREFOR

CROSS-REFERENCE TO RELATED APPLICATION

This application claims priority to U.S. Provisional Application Ser. Nos. 61/982,049 and 61/982,091, both filed on Apr. 21, 2014, and U.S. Provisional Application Ser. No. 62/050,930 filed on Sep. 16, 2014, which are each hereby incorporated by reference in their entirety.

BACKGROUND OF THE INVENTION

Field of the Invention

The present invention relates to a fluid transfer device for a closed transfer of fluid from a medical device to a patient delivery device, such as an IV line or syringe. More specifically, the invention is directed to a fluid transfer device and packaging therefor configured for engaging/disengaging a connection element on the fluid transfer device using the packaging.

Description of Related Art

Healthcare workers, such as pharmacists and nurses, can be subject to acute and long term health risks upon repeated exposure to drugs or solvents which might escape into the air during drug preparation, drug administration, and other similar handling. This problem is particularly serious when cytotoxins, antiviral drugs, antibiotics, and radiopharmaceuticals are concerned. The health risks faced by exposure to these drugs can include the development of cancer, reproductive problems, genetic conditions, and other serious concerns. Other hazardous areas may be sample taking, such as samples concerning virus infections or the like. When performing infusions, it is often necessary to inject a drug or other medical substance into the infusion fluid, inside an infusion bag or other infusion fluid container. This is often done by means of penetrating a septum or other fluid barrier of an injection port on the infusion bag or on the infusion fluid line with a needle of a syringe filled with the medical fluid in question. However, even before this, it may be necessary to transfer the medical fluid from a vial to a syringe and then from the syringe to a secondary container. In each of these steps, staff may be exposed to the medical fluid by means of contamination. Such contamination may be vaporized medical fluid or aerosol in the air. The contaminations may contaminate the staff through their lungs, or by vaporized medical fluid or aerosol in the air which condensates on the skin to thereafter penetrate the skin of the staff. Some medicaments are even known to penetrate protection gloves and thereby contaminate the staff.

Exposure to contaminations like this may, on a long term basis, give rise to alarmingly high concentrations of medicaments in the blood or the human body of the staff as described above. It has been understood that, due to the many transferring steps between containers e.g., vials, syringes, infusion systems, etc., the risk for contamination during the actual insertion and retraction of a needle from the container, e.g., a vial, needs to be contained. Closed system transfer devices (CSTDs) have been developed to ensure that the medicament is contained in the transfer device during transfer of the medicament.

Generally, a CSTD includes an adapter for connection to a syringe and an adapter for connection to a vial, a second syringe, or a conduit providing fluid access to the patient's circulatory system. According to one arrangement, the healthcare practitioner may reconstitute a powdered or lyophilized compound with saline or some other reconstitution medium by attaching the syringe to the vial via connection of the respective adapters, reconstituting the drug, aspirating the compound into the syringe, disconnecting the adapters, and then attaching the syringe to the fluid conduit through the respective adapters to a patient delivery device, such as an IV line or syringe for administration to the patient.

One type of an adapter that can be used in a CSTD has a first connector having a male or female luer-lock element that is arranged to be joined with a corresponding female or male luer-lock element of a second connector component. According to one aspect, the second connector component can be a patient delivery device, such as an IV line or a syringe. The luer-lock element can, thus, be screwed into and unscrewed from the corresponding luer-lock element. It is desirable to prevent an accidental or inadvertent unscrewing of the components, which could lead to the disconnection of the fluid passage. Such disconnection may entail a serious contamination risk for a patient and/or any other person in the vicinity of the disconnected medical connector. The issue of safety in administration of hazardous medical compounds is one that has been identified as being of critical importance by professional organizations and government agencies alike.

It is, therefore, desirable to provide an adapter for enabling fluid transfer between the first connector and the second connector by facilitating a positive connection of the connectors and avoiding inadvertent or accidental disconnection of the connectors.

SUMMARY OF THE INVENTION

In one aspect of the present invention, a fluid transfer system includes packaging having a body with a sidewall extending between an open top end and a bottom end and defining an interior cavity, and at least one protrusion extending radially inward from the sidewall into the interior cavity. The system also includes a fluid transfer device configured to be received within the interior cavity and including an inner member configured to be secured to a container and an outer member surrounding at least a portion of the inner member. The inner member having a first position where the inner member is configured to rotate freely relative to the outer member and a second position where rotation of the inner member relative to the outer member is restricted in a first rotational direction. The fluid transfer device also including a locking arrangement provided on at least a portion of the inner member and accessible through at least a portion of the outer member. The locking arrangement is configured for cooperating with the at least one protrusion to prevent rotation of the inner member relative to the outer member upon an application of a compressive force on the packaging.

The at least one protrusion may be a pair of protrusions that are oriented opposite from each other around a circumference of the packaging. The packaging may further include at least one button extending radially outward from an outer portion of the sidewall opposite the at least one protrusion. The at least one protrusion may be configured to deflect radially inward in response to the compressive force directed to the at least one button.

The outer member of the fluid transfer device may define an opening configured to receive the at least one protrusion of the packaging when the fluid transfer device is positioned within the interior cavity of the packaging. The at least one protrusion of the packaging and the opening of the outer member of the fluid transfer device may cooperate to prevent rotation of the fluid transfer device relative to the packaging when the fluid transfer device is positioned within the interior cavity of the packaging.

The at least one protrusion of the packaging may be configured to engage the locking arrangement through the opening in the outer member of the fluid transfer device to prevent rotation of the inner member relative to the outer member when the fluid transfer device is positioned within the interior cavity of the packaging.

The locking arrangement may be a recess defined by the inner member, with the recess having an engagement surface configured to engage the at least one protrusion of the packaging. The inner member may be a luer connection.

The inner member and the outer member may define a ratchet arrangement, where the ratchet arrangement is only engaged when the inner member is in the second position. The inner member may be moveable in an axial direction within the outer member between the first and second positions of the inner member.

The packaging may define a plurality of ribs extending radially inward from the sidewall of the packaging, with the plurality of ribs configured to engage a portion of the fluid transfer device when the fluid transfer device is positioned within the interior cavity of the packaging.

The fluid transfer system may further include a seal arrangement positioned within the outer member, with the seal arrangement moveable within the outer member and configured to engage a mating connector. The seal arrangement having an actuated position adjacent to the inner member and an initial position spaced from the inner member, where the seal arrangement prevents the inner member from moving from the first position to the second position when the seal arrangement is in the actuated position. The inner member and the outer member may define a ratchet arrangement, where the ratchet arrangement is only engaged when the inner member is in the second position.

In a further aspect of the present invention, a fluid transfer device includes an inner member configured to be secured to a container and an outer member surrounding at least a portion of the inner member. The inner member having a first position where the inner member is configured to rotate freely relative to the outer member and a second position where rotation of the inner member relative to the outer member is restricted in a first rotational direction. The device further includes a seal arrangement positioned within the outer member. The seal arrangement is moveable within the outer member and configured to engage a mating connector. The seal arrangement having an actuated position adjacent to the inner member and an initial position spaced from the inner member, where the seal arrangement prevents the inner member from moving from the first position to the second position when the seal arrangement is in the actuated position.

The inner member and the outer member may define a ratchet arrangement, where the ratchet arrangement is only engaged when the inner member is in the second position.

The device may further include a locking arrangement provided on at least a portion of the inner member and accessible through at least a portion of the outer member. The inner member may be moveable in an axial direction within the outer member between the first and second positions of the inner member. The locking arrangement may be a recess defined by the inner member, the recess having an engagement surface.

In another aspect of the present invention, a patient connector and packaging includes a patient connector having a body and at least one protrusion extending radially outward from the body, and packaging having an open first end, a second end, and a sidewall extending between the first and second ends. The packaging includes a plurality of guide protrusions positioned adjacent to the first end of the packaging. The at least one protrusion is configured to be received between the plurality of guide protrusions of the packaging.

DETAILED DESCRIPTION

Figure 1:
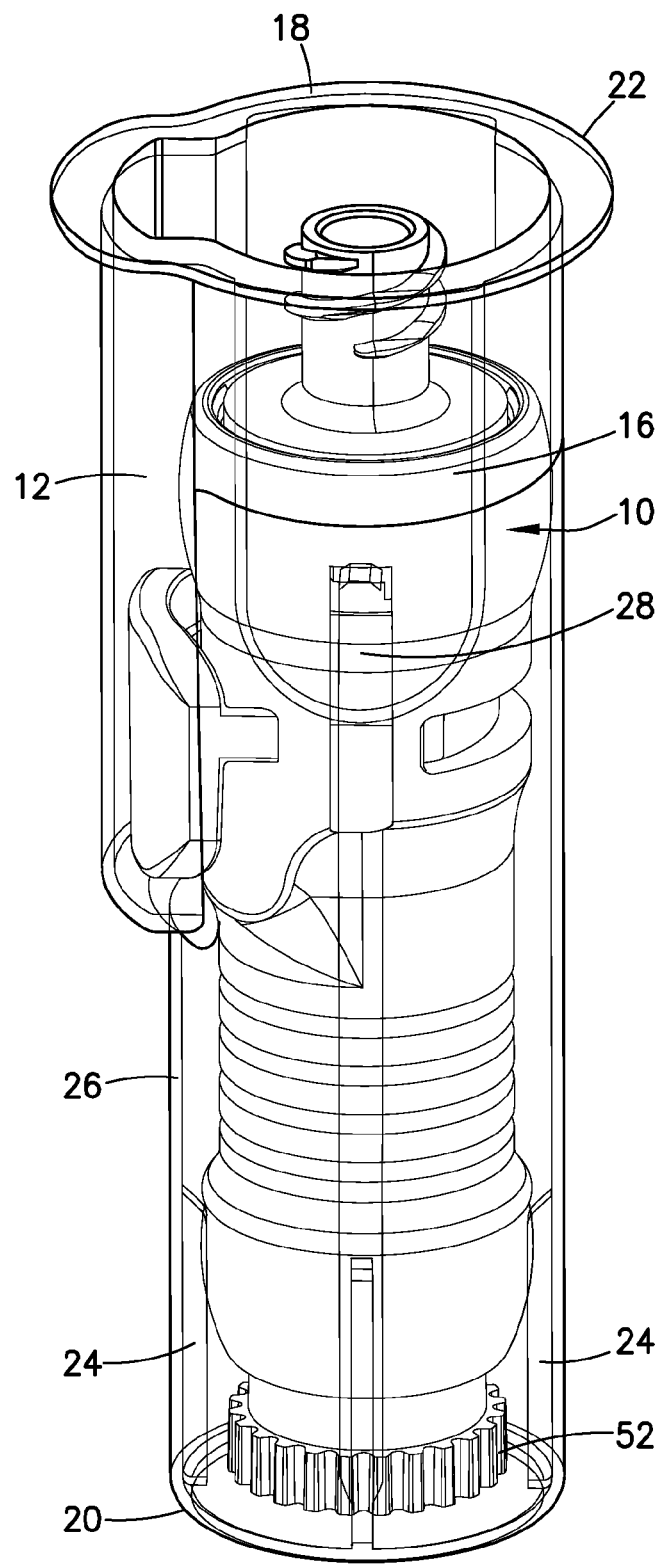
FIG. 1 is a perspective view of a fluid transfer device and packaging according to one aspect of the present invention.

The illustrations generally show preferred and non-limiting aspects of the systems and methods of the present disclosure. While the descriptions present various aspects of the devices, it should not be interpreted in any way as limiting the disclosure. Furthermore, modifications, concepts, and applications of the disclosure's aspects are to be interpreted by those skilled in the art as being encompassed by, but not limited to, the illustrations and descriptions herein.

Further, for purposes of the description hereinafter, the terms "end", "upper", "lower", "right", "left", "vertical", "horizontal", "top", "bottom", "lateral", "longitudinal", and derivatives thereof shall relate to the disclosure as it is oriented in the drawing figures. The term "proximal" refers to the direction toward the center or central region of the device. The term "distal" refers to the outward direction extending away from the central region of the device. However, it is to be understood that the disclosure may assume various alternative variations and step sequences, except where expressly specified to the contrary. It is also to be understood that the specific devices and processes illustrated in the attached drawings, and described in the following specification, are simply exemplary aspects of the disclosure. Hence, specific dimensions and other physical characteristics related to the aspects disclosed herein are not to be considered as limiting. For the purpose of facilitating understanding of the disclosure, the accompanying drawings and description illustrate preferred aspects thereof, from which the disclosure, various aspects of its structures, construction and method of operation, and many advantages may be understood and appreciated.

Referring to FIGS. 1-17, a fluid transfer device 10 and packaging 12 for the fluid transfer device 10 is shown in accordance with one aspect of the invention. The fluid transfer device 10 facilitates the transfer of fluid between a first container (not shown), such as a syringe, and a second container, such as a vial, IV bag, IV line, etc. The fluid transfer device 10 facilitates such transfer while ensuring fluid does not leak from the fluid transfer device 10. As discussed in more detail below, the packaging 12 holds the fluid transfer device 10 prior to use and functions to allow removal of a container, such as a syringe, from the fluid transfer device 10 after attachment thereto. In particular, as discussed below, the fluid transfer device 10 includes features that inhibit disconnection of a container from the fluid transfer device 10 to prevent accidental leakage of fluid from the device 10 and the packaging 12 may be utilized to allow the intentional removal of a container from the fluid transfer device 10.

Figure 2:
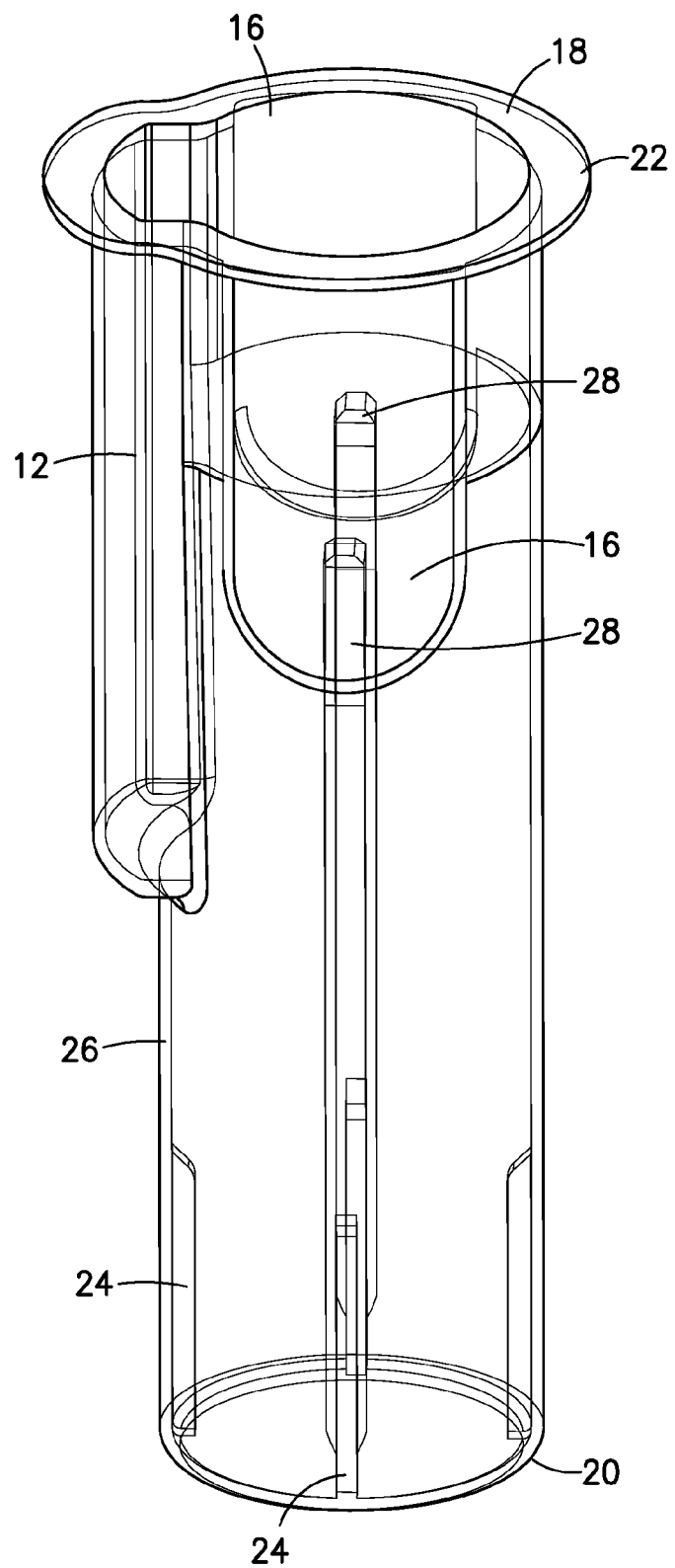
FIG. 2 is a perspective view of packaging for a fluid transfer device according to one aspect of the present invention.
Figure 3:
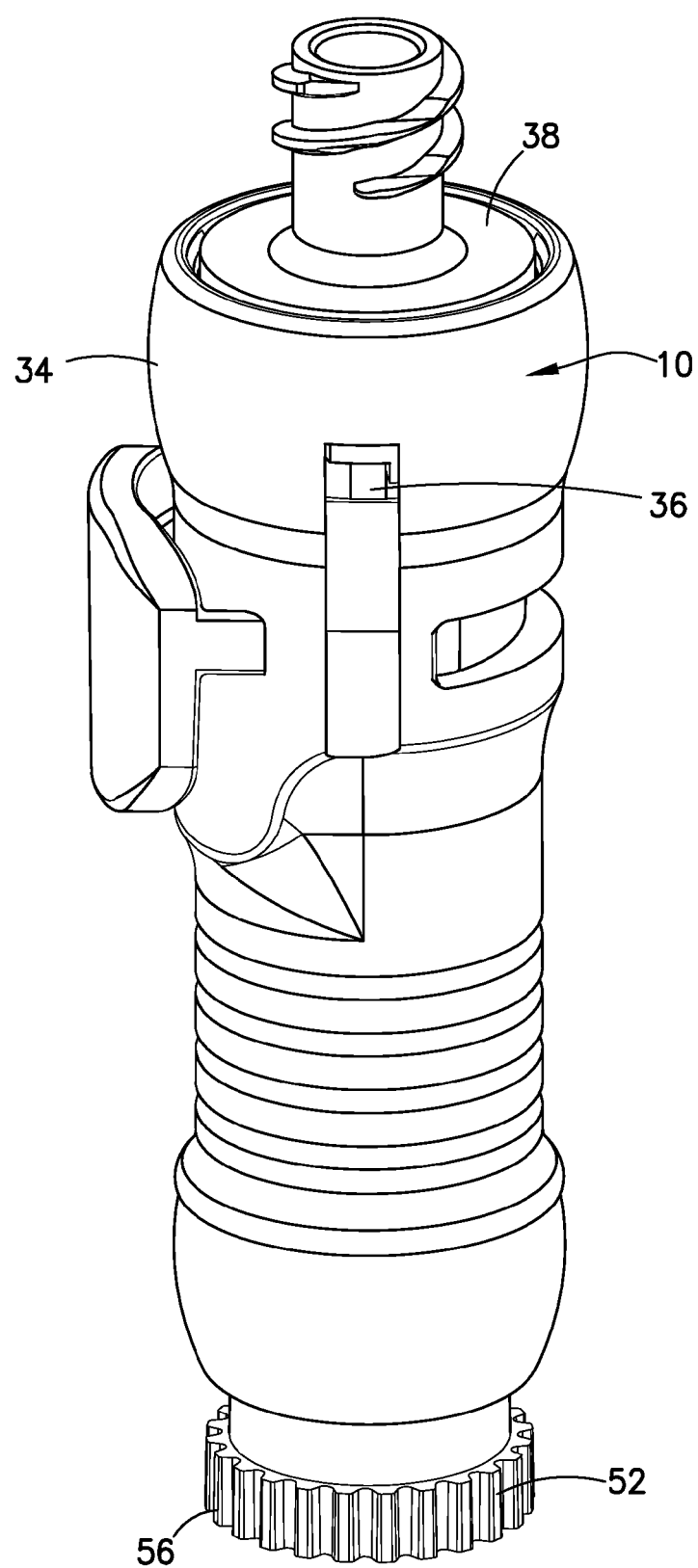
FIG. 3 is a perspective view of a fluid transfer device according to one aspect of the present invention.
Figure 4:
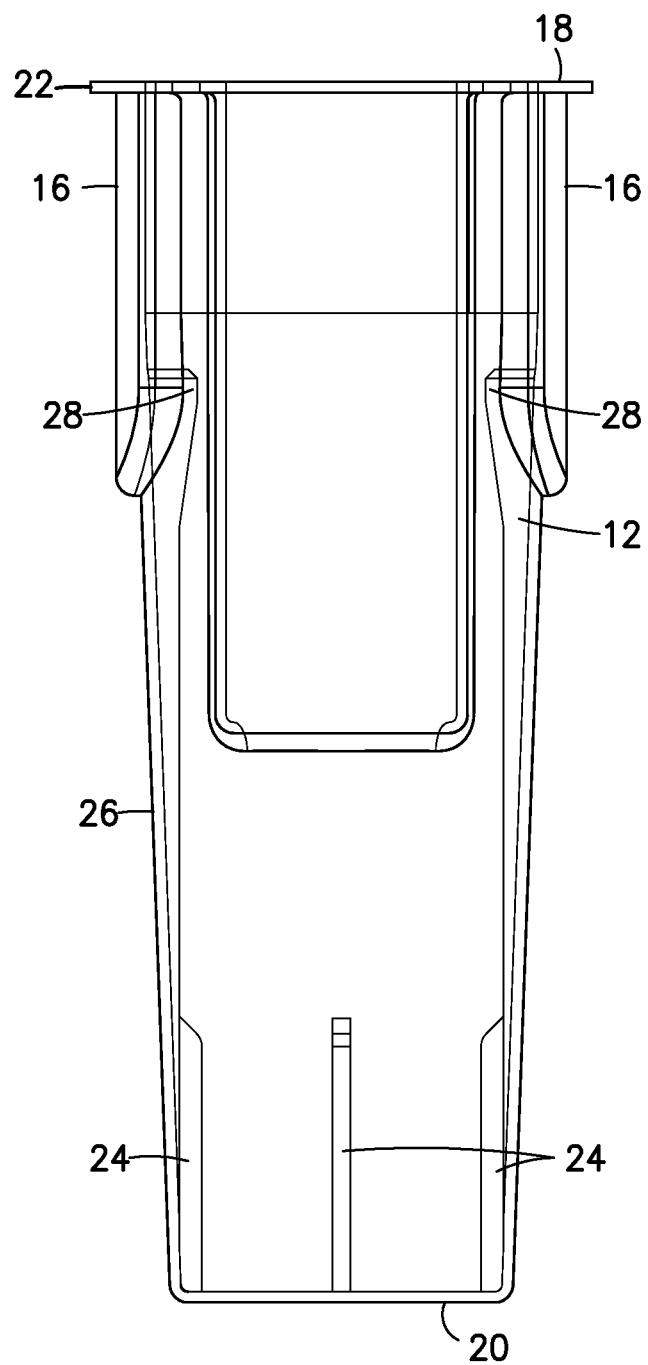
FIG. 4 is a front view of the packaging of FIG. 2.
Figure 5:
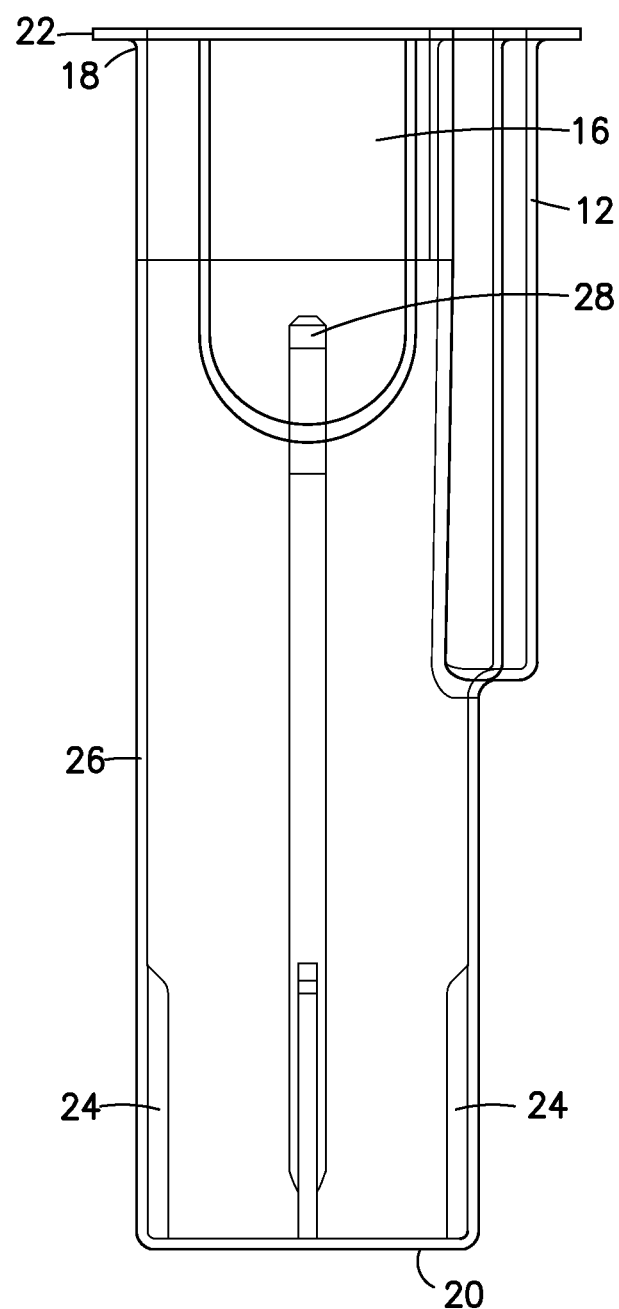
FIG. 5 is a right side view of the packaging of FIG. 2.
Figure 6:
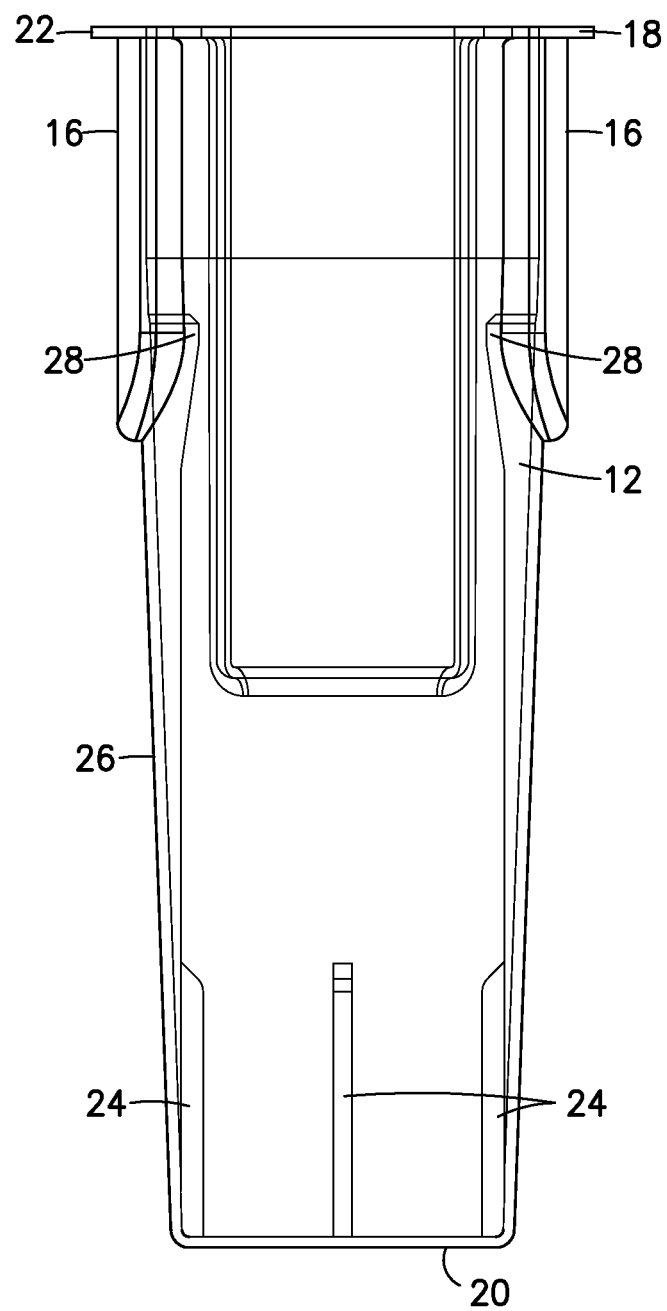
FIG. 6 is a rear view of the packaging of FIG. 2.
Figure 7:
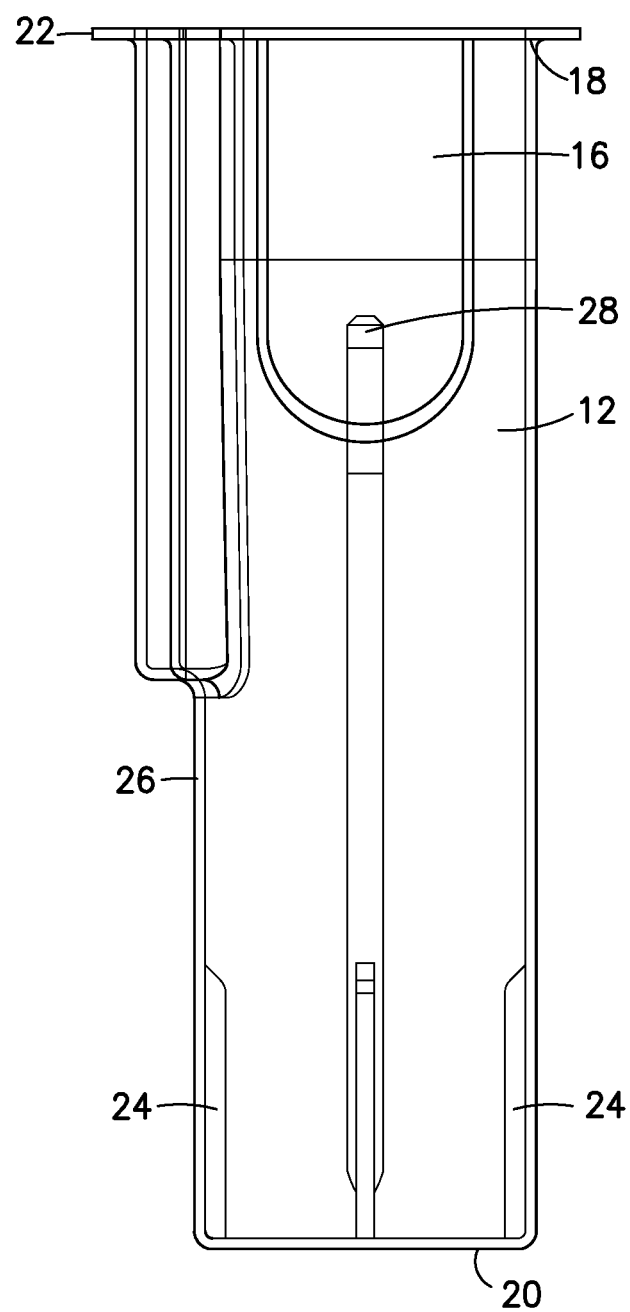
FIG. 7 is a left side view of the packaging of FIG. 2.
Figure 8:
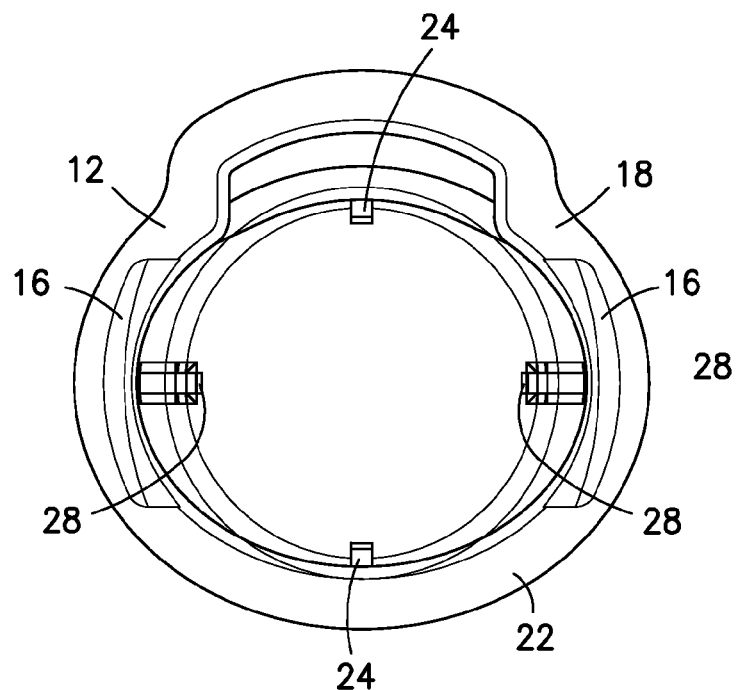
FIG. 8 is a top view of the packaging of FIG. 2.
Figure 9:
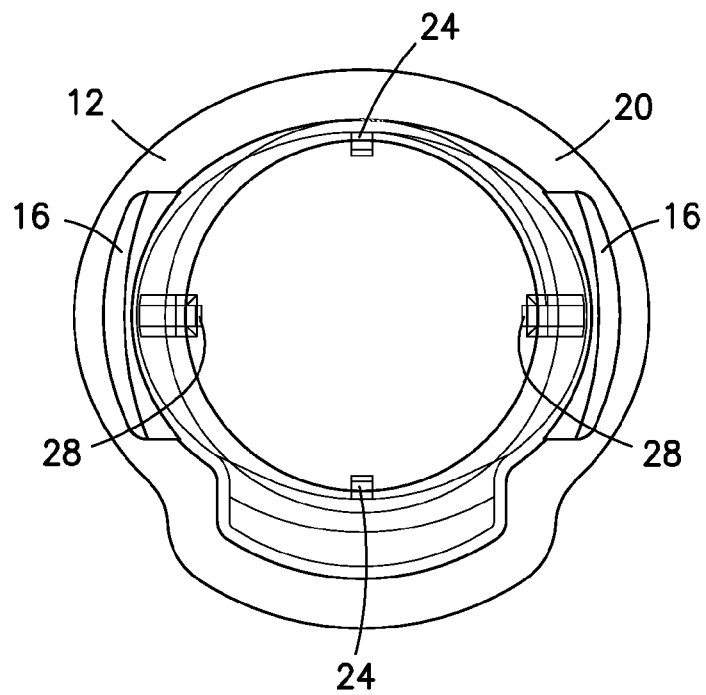
FIG. 9 is a bottom view of the packaging of FIG. 2.

Referring to FIGS. 1, 2, and 4-9, the packaging 12 is shown as transparent, although the packaging 12 may or may not be made from a transparent or semi-transparent material. The packaging 12 defines an interior cavity 14 and includes elongate buttons 16 that extend from a position intermediate first and second ends 18, 20 of the packaging 12 to a flange 22 at the first end 18 of the packaging 12. The elongate buttons 16 provide a larger surface area for a user to engage during use the packaging 12 compared to circular buttons or tabs. As shown in FIGS. 1 and 2, the packaging 12 also includes a plurality of ribs 24 protruding from a sidewall 26 of the packaging 12 radially inward. The plurality of ribs 24 extend longitudinally from the second end 20 of the packaging 12 towards the first end 18 of the packaging 12. The plurality of ribs 24 are configured to engage a portion of the fluid transfer device 10 to prevent movement of the fluid transfer device 10 within the packaging 12 until a user purposefully removes the fluid transfer device 10 from the packaging 12. In particular, the plurality of ribs 24 may prevent the fluid transfer device 10 from sliding axially within the packaging 12, which can cause damage and wear to the closure (not shown) of the packaging 12.

The packaging 12 also includes projections 28 extending radially inward from the sidewall 26 that are configured to move radially inward upon engagement of the elongate buttons 16. The projections 28 extend in a direction substantially parallel to the longitudinal axis of the packaging 12. In certain aspects, the projections 28 may be angled relative to the longitudinal axis. The projections 28 may have any desired shape, including, but not limited to, square, rectangular, rounded, etc. In one aspect, the projections 28 extend from a region of the inner sidewall 26 proximate to the closed bottom end 20 to an area of the inner sidewall 26 opposite the elongate buttons 16. The projections 28 may be oriented 180 degrees apart around a circumference of the packaging 12 such that each projection 28 is aligned with the elongate button 16. For example, the longitudinal midpoint of each projection 28 may be aligned with an axis extending through the center of each elongate button 16. The projections 28 may define an alignment feature for aligning the fluid transfer device 10 within the interior cavity 14 of the packaging 12. The projections 28 are configured to deflect radially inward in response to a radially-directed force imparted on the elongate buttons 16. Although the projections 28 are separated equally about the circumference of the packaging 12, it is to be appreciated that more than two projections 28 may be provided with equal or unequal separation about the circumference of the container 10.

The packaging 14 may be constructed from any known material, such as a molded, injected, or thermo-formed plastic material. Desirably, the packaging 14 is constructed from a material that provides flexibility of the sidewall 26 in at least the radial direction with respect to the longitudinal axis. In particular, the packaging 14 is desirably constructed from a material that allows the cross-sectional shape of the packaging 14 to change with an application of a radially-directed force, as will be described in greater detail below.

Referring to FIGS. 1, 2, and 4-9, the packaging 12 further includes a recess 32 that is configured for receiving an activation tab of the fluid transfer device 10, as will be described hereinafter. The recess 32 extends radially outward relative to the longitudinal axis of the packaging 12. The recess 32 also extends along at least a portion of the longitudinal length of the packaging 12. The recess 32 is shaped such that the sidewall 26 bulges radially outward in the area of the recess 32. In addition to accommodating a portion of the fluid transfer device 10, the recess 32 also orients the fluid transfer device 10 such that it can be received in the interior cavity 14 in one direction only. Other features of the fluid transfer device 10 or the packaging 12 may be used to align the fluid transfer device 10 within the interior cavity 14 of the container 10.

Referring to FIGS. 1, 3, and 10-17, the fluid transfer device 10 includes an outer member 34 defining openings 36 that are configured to receive at least a portion of the projections 28 of the packaging 12. Further, the fluid transfer device 10 includes an inner member 38 having recesses 40 and engagement surfaces 42 that are configured to cooperate with the projections 28 of the packaging 12 to restrict relative movement of the inner member 38 relative to the outer member 34 as discussed in more detail below. The inner member 38 is embodied as a luer body, although any other suitable connection arrangements may be utilized. The fluid transfer device 10 also includes a ratchet arrangement 44 formed by portions of the inner member 38 and the outer member 34. The inner member 38 is moveable in an axial direction relative to the outer member 34 and includes ratchet teeth 46 configured to cooperate with corresponding shaped projections 48 on the outer member 34. The inner member 38 has a first axial position where the inner member 38 is free to rotate relative to the outer member 34 and a second axial position where the ratchet teeth 46 are engaged with the projections 48 of the outer member 34 to restrict relative movement between the inner member 38 and the outer member 34 in a single rotational direction. Thus, when the inner member 38 is in the second axial position, the inner member 38 will be able to rotate relative to the outer member 34 is one rotational direction, but restricted from moving relative to the outer member 34 is an opposite rotational direction.

Figure 12:
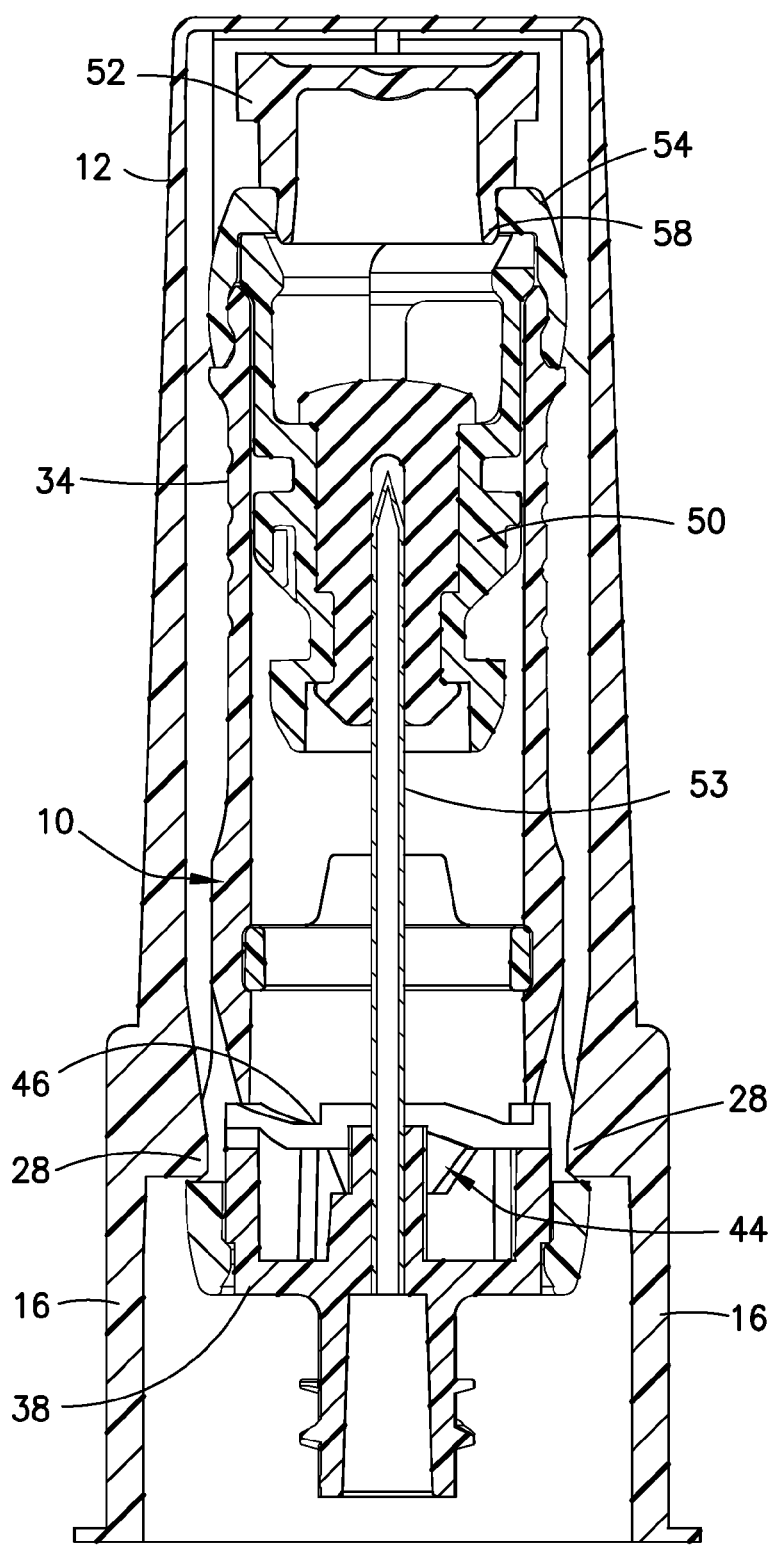
FIG. 12 is a cross-sectional view of the fluid transfer device and packaging of FIG. 1.
Figure 14:
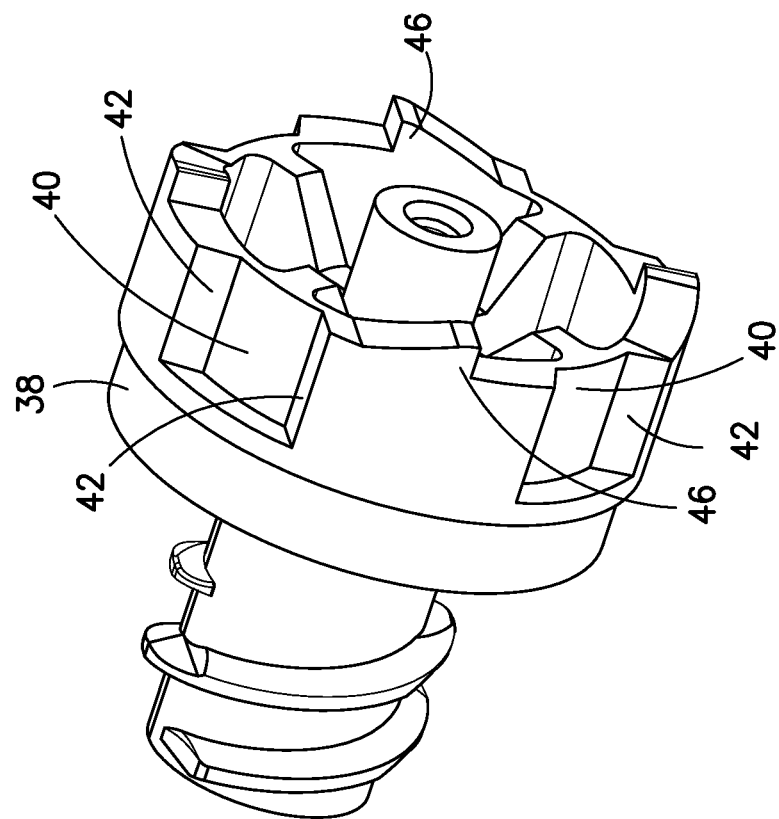
FIG. 14 is a perspective view of the luer body of FIG. 13.
Figure 13:
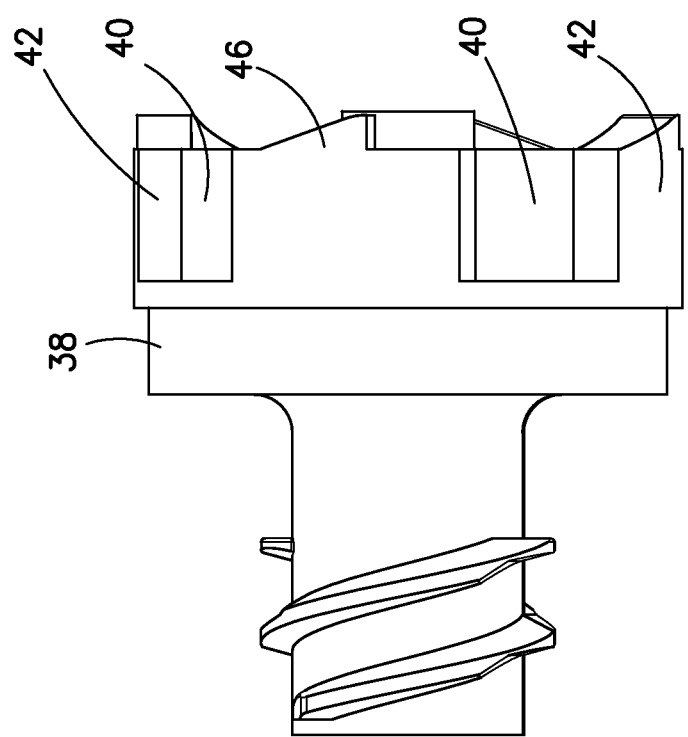
FIG. 13 is a side view of a luer body of the fluid transfer device of FIG. 3.
Figure 15:
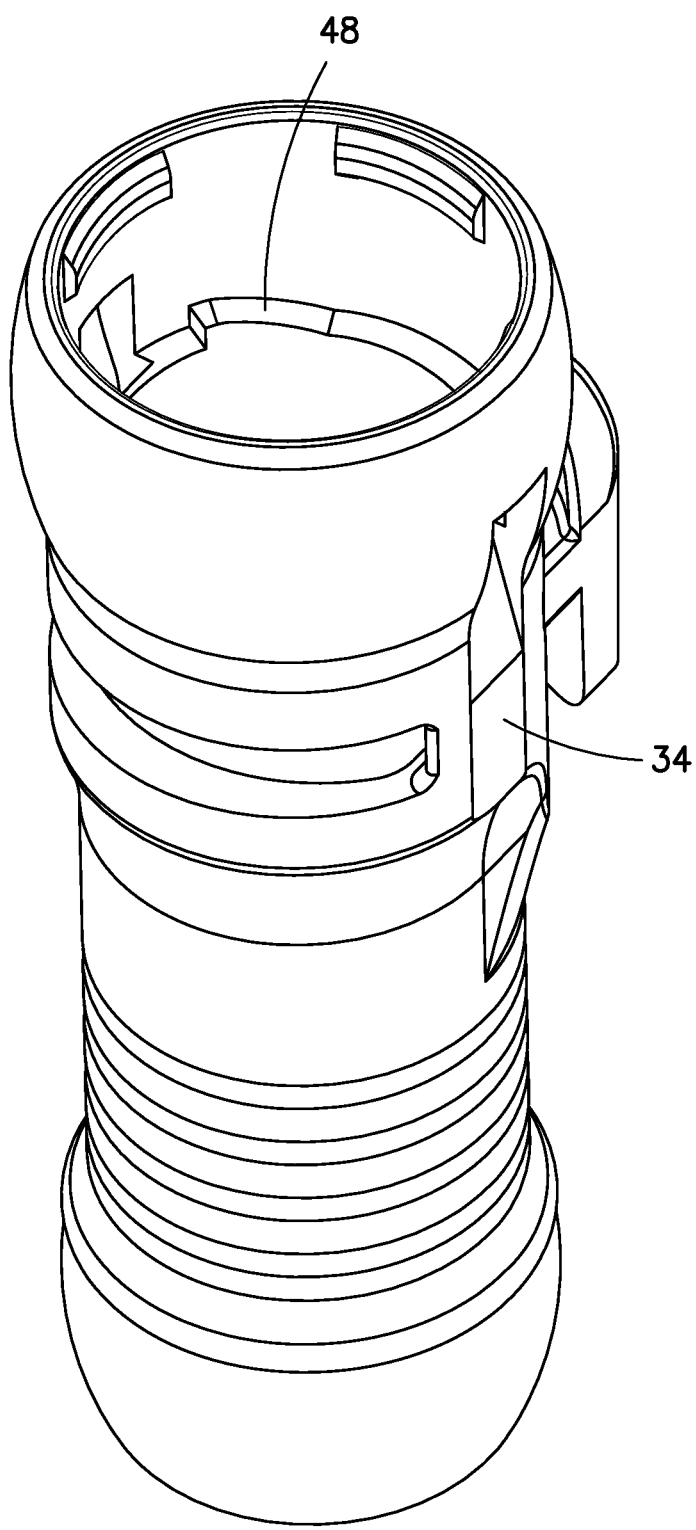
FIG. 15 is a perspective view of a body of the fluid transfer device of FIG. 3.
Figure 16:
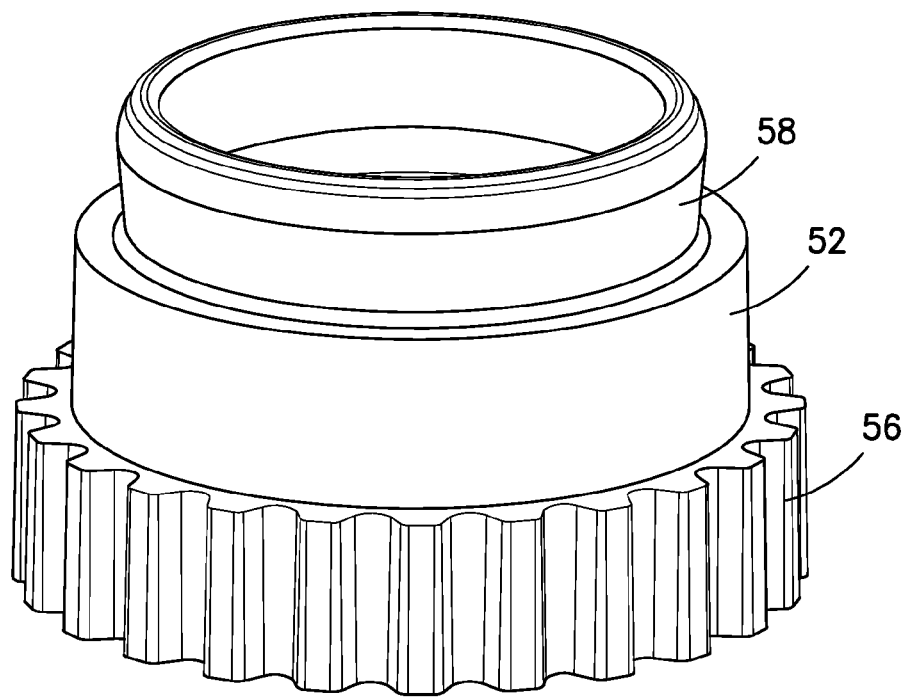
FIG. 16 is a perspective view of a cap of the fluid transfer device of FIG. 3.
Figure 17:
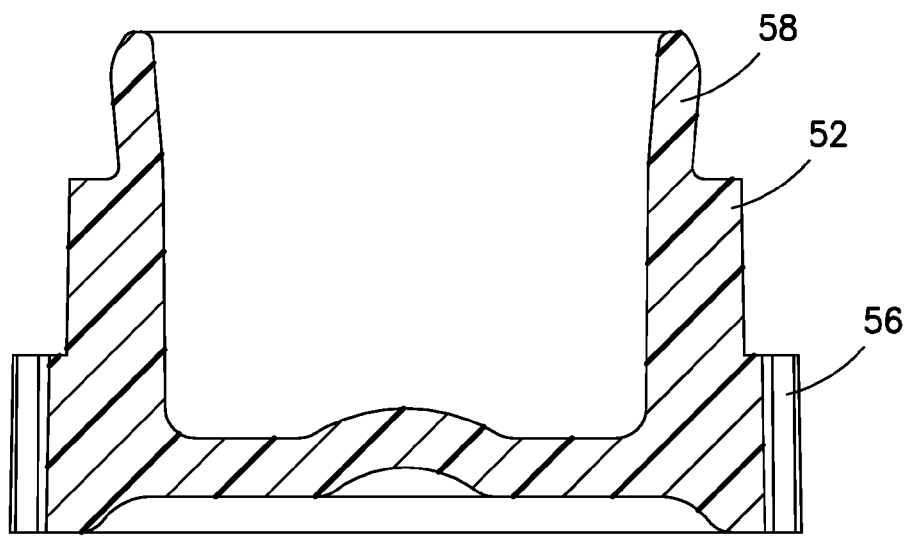
FIG. 17 is a cross-sectional view of the cap of FIG. 16.
Figure 18:
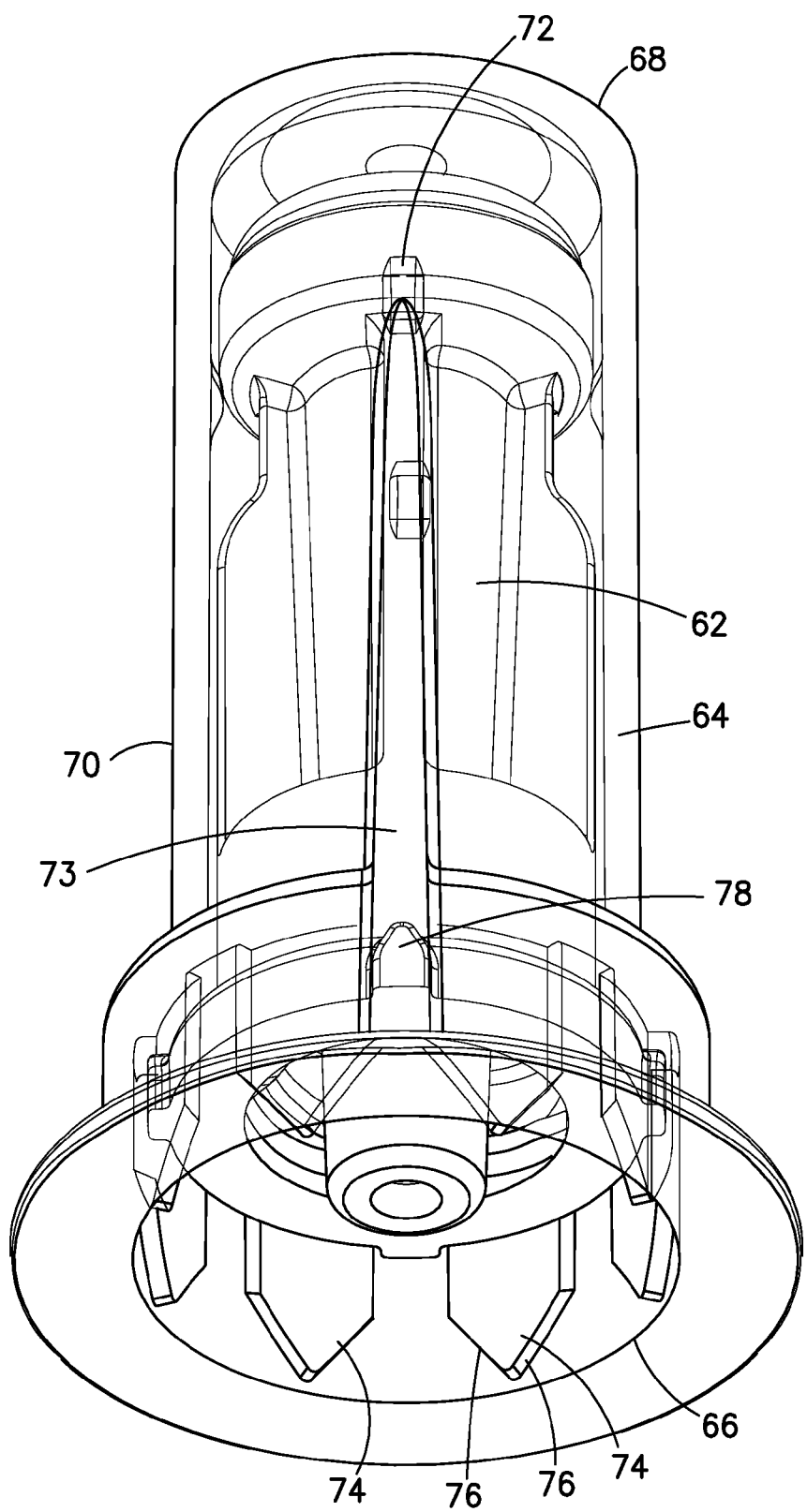
FIG. 18 is a perspective view of a patient connector and packaging according to one aspect of the present invention.
Figure 19:
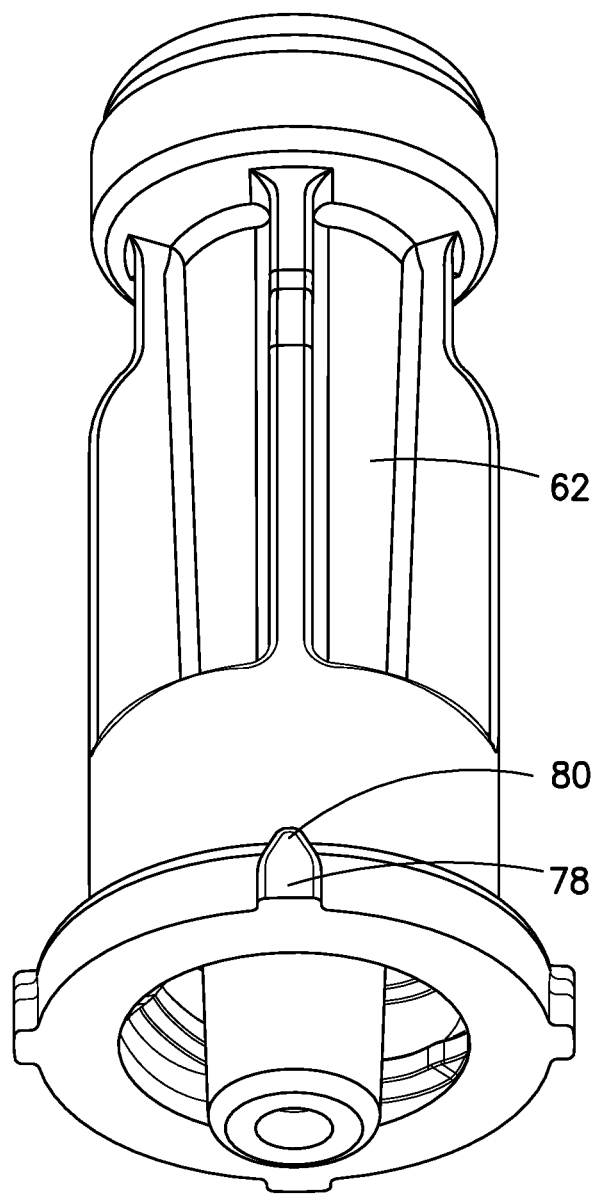
FIG. 19 is a perspective view of a patient connector according to one aspect of the present invention.
Figure 20:
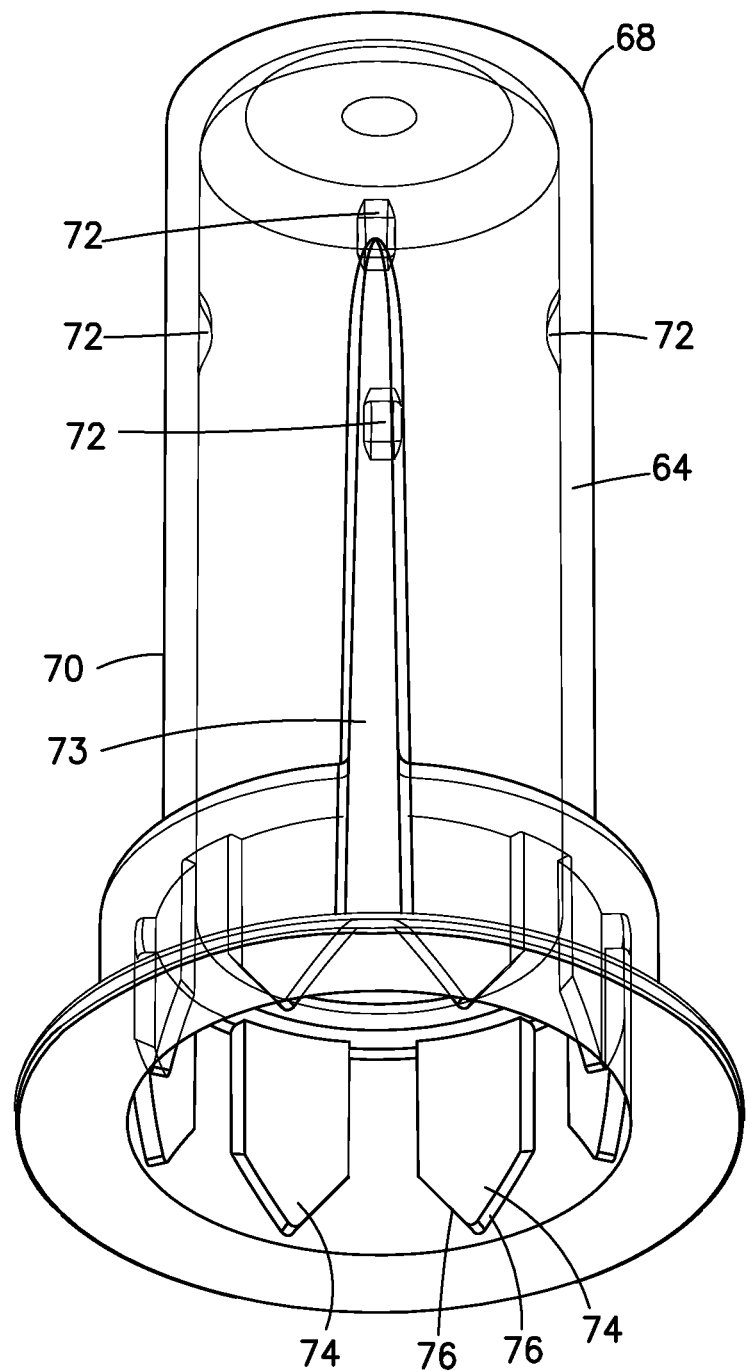
FIG. 20 is a perspective view of packaging for a patient connector according to one aspect of the present invention.
Figure 21:
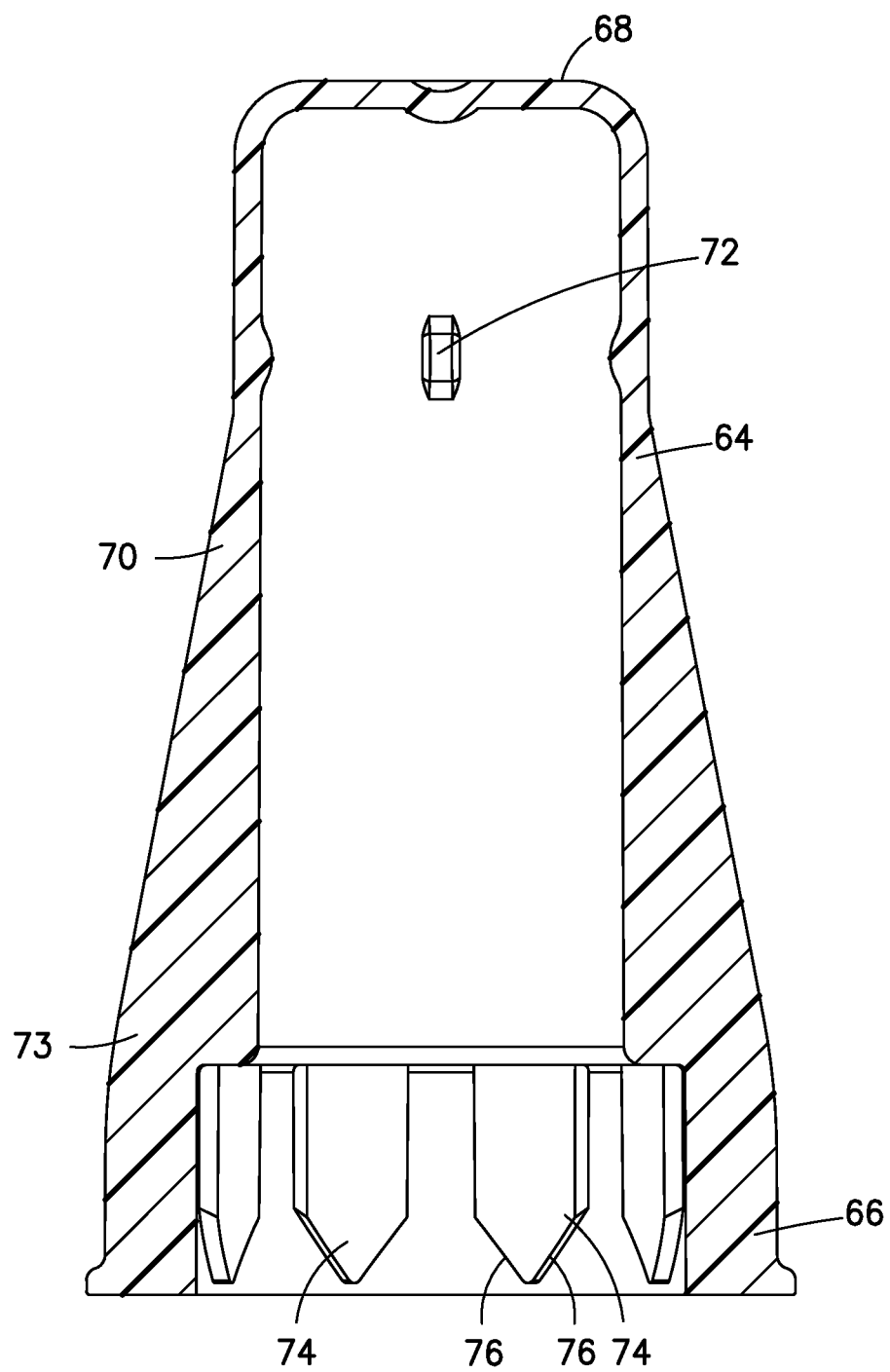
FIG. 21 is a cross-sectional view of the packaging of FIG. 20.

Referring to FIGS. 1 and 12, in order to attach a container, such as a syringe barrel, to the inner member 38, an axial force must be applied to the inner member 38 to move the inner member 38 from the first position to the second position, which will engage the ratchet arrangement 44 to prevent relative rotation between the inner and outer members 38, 34 to allow the container to be secured to the inner member 38. During this attachment, a portion of the projections 28 of the packaging 12 will contact a portion of the outer member 34 to provide resistance to torque created by the attachment to prevent rotation of the fluid transfer device 10 relative to the packaging 12. Any portion of the fluid transfer device 10 may interface with a corresponding portion of the packing 12 to prevent rotation of the fluid transfer device 10 relative to the packaging 12 to readily allow attachment to the inner member 38.

The axial force may be a slight nudge of the inner member 38, although any other suitable axial force may be utilized. Rotation in an opposite direction to remove the container from the fluid transfer device 10, however, will not engage the ratchet arrangement 44 and the inner member 38 will merely rotate within the outer member 34 due to the sloped surface of the ratchet teeth 46. Thus, a container cannot be removed from the inner member 38 of the fluid transfer device 10 when the inner member 38 is in the first or second position without the use of the packaging 12. The container can be removed from the fluid transfer device 10 by inserting the fluid transfer device 10 into the packaging 12 and engaging the elongate buttons 16 of the packaging 12 such that the projections 28 of the packaging 12 are received by the engagement surfaces 42 to lock the inner member 38 relative to the outer member 34. With the inner member 38 locked or rotationally fixed relative to the outer member 34, the container can be removed from the inner member 38 of the fluid transfer device 10.

Figure 10:
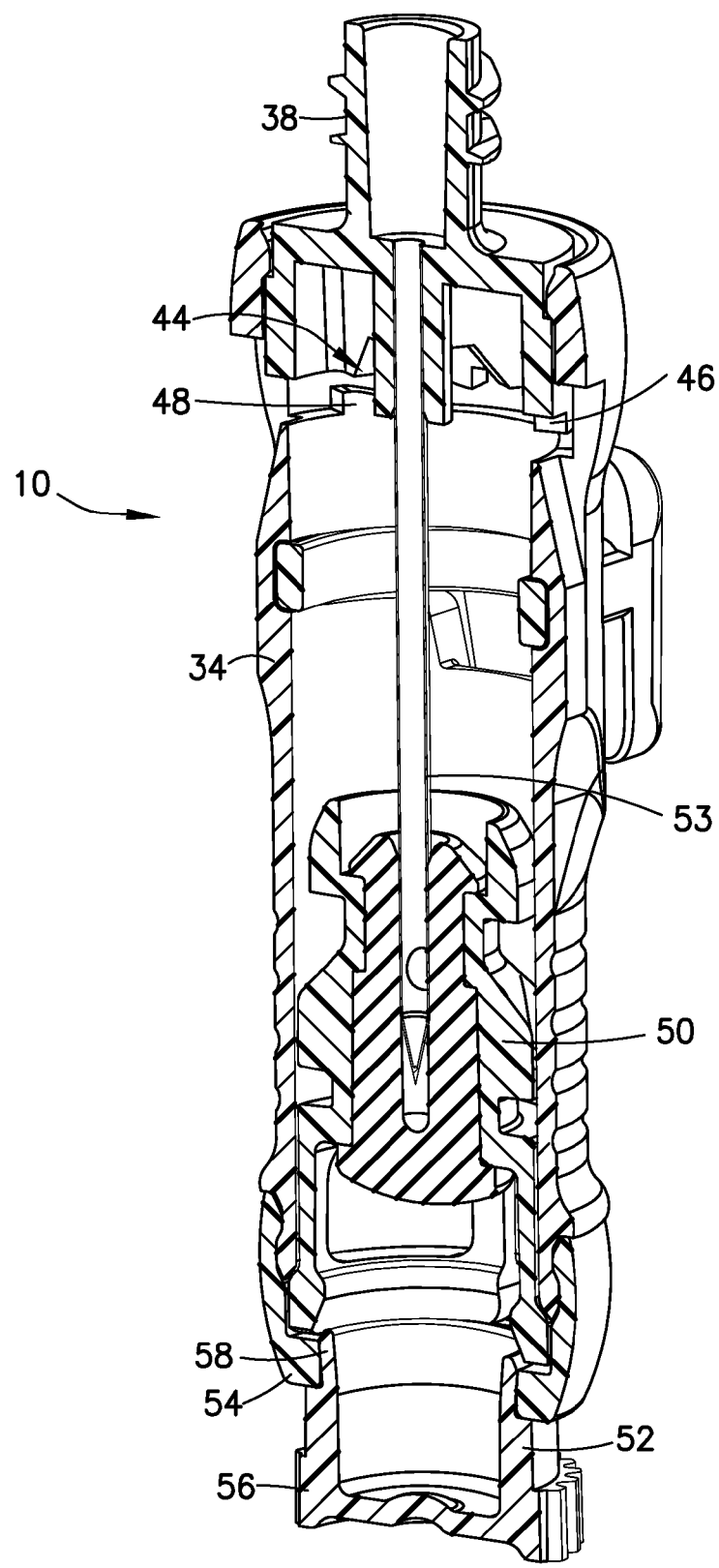
FIG. 10 is a perspective cross-sectional view of the fluid transfer device of FIG. 3.
Figure 11:
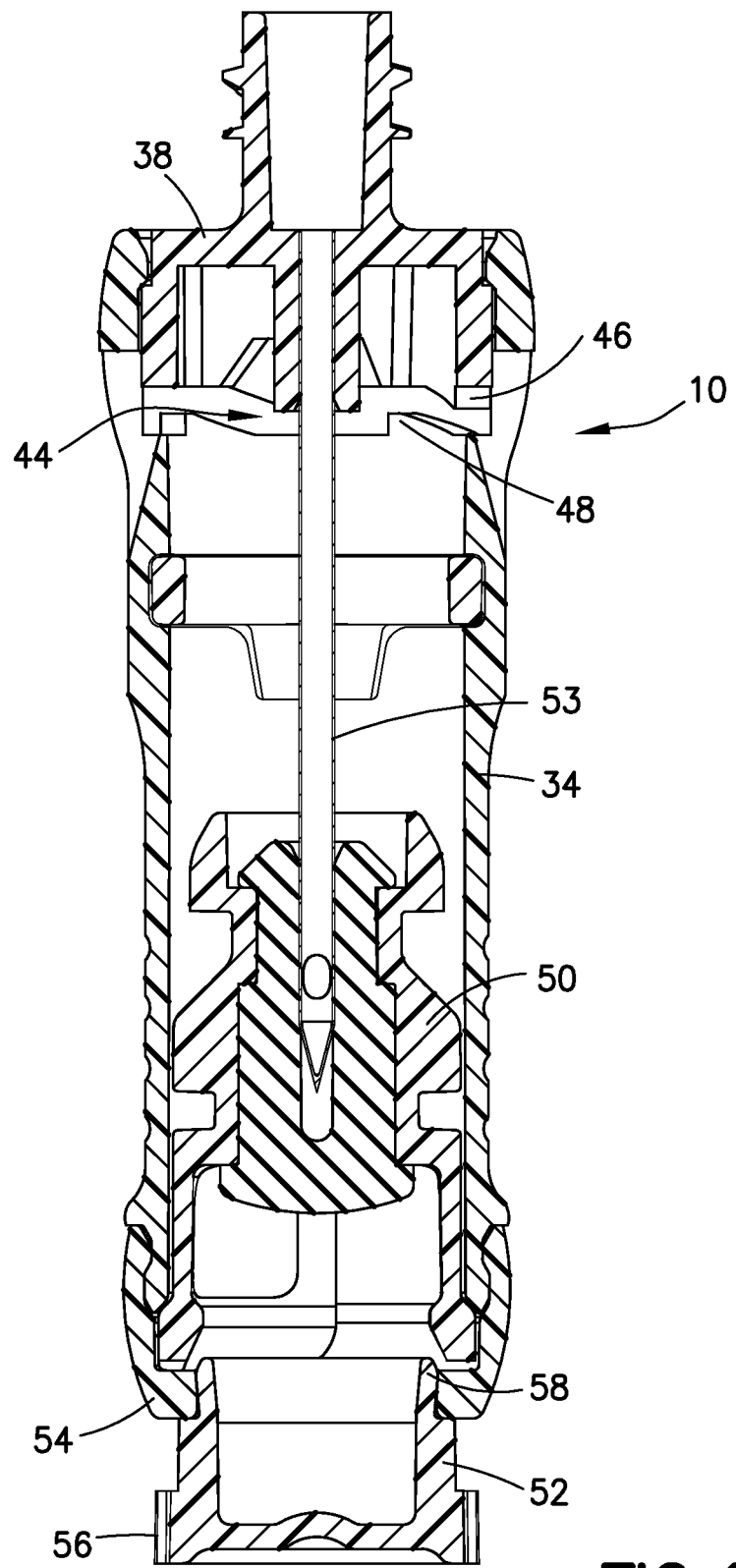
FIG. 11 is a cross-sectional view of the fluid transfer device of FIG. 3.

Referring to FIGS. 10-12, the fluid transfer device 10 includes a seal arrangement 50, such as a collet and membrane assembly shown in FIGS. 10-12, that cooperates with a mating connector and moves within the outer member 34 to provide for the sealed transfer of fluids using the fluid transfer device 10 as discussed above. The fluid transfer device 10 also include a cannula 53 secured to the inner member 38 that is configured to pierce the membrane of the seal arrangement 50 and the membrane of the mating connector during the sealed transfer of fluids using the device 10. The seal arrangement 50 also secures the fluid transfer device 10 to the mating connector or component during the transfer of fluids. The fluid transfer device 10 may further include a secondary arrangement for ensuring the device 10 is secured to the mating connector or component during fluid transfer. In particular, the fluid transfer device may include an activation tab 51 provided in an opening of the outer member 34 and extending perpendicularly through the outer member 34. The activation tab 51 cooperates with the seal arrangement 50 and is secured to the seal arrangement 50 when the seal arrangement 50 is in an actuation position adjacent to the inner member 38 to maintain the seal arrangement 50 in that position. In such a position, the mating connector or component that is mated with the seal arrangement 50 cannot be disconnected from the fluid transfer device 10. The mating connector or component can be disengaged from the fluid transfer device 10 by pushing or engaging the activation tab 51 radially inward, which allows the mating connector to move the seal arrangement 50 thereby allowing the mating connector to be withdrawn from the outer member 34 of the fluid transfer device 10. Further, the activation tab 51 may interface with the recess 32 of the packaging 12 to prevent rotation of the fluid transfer device 10 relative to the packaging 12 while attachment of the container to the inner member 38 is made.

Referring again to FIGS. 10-12, in one aspect of the present invention, the fluid transfer device 10 also includes a lift-off feature that restricts the movement of the inner member 38 from the first position to the second position. In one position, such as when the fluid transfer device 10 is connected to a mating connector or component, the seal arrangement 50 is in an actuation position adjacent to the inner member 38. In this position, the seal arrangement 50 prevents the inner member 38 from moving from the first position to the second position described above. Accordingly, the seal arrangement 50 prevents the ratchet arrangement 44 from being engaged. In other words, the seal arrangement 50 abuts the inner member 38 to prevent the inner member 38 from moving to the second position where the ratchet teeth 46 can engage the projections 48. Although the ratchet arrangement 44 only allows for tightening of a container, such as a syringe, onto the inner member 38, an alternative arrangement may be provided that allows disconnection and/or connection of a syringe to the inner member 38 when the inner member 38 is in the second position, which can be deactivated via the lift-off feature described above.

Referring to FIGS. 1, 10-13, 17, and 18, the fluid transfer device 10 also includes a cap 52 configured to close an end 54 of the fluid transfer device 10. The cap 52 includes a gripping surface 56 and a tapered insertion end 58 that is received by the fluid transfer device 10. The tapered insertion end 58 may deflect radially inward upon insertion into the fluid transfer device 10 to secure the cap 52 to the fluid transfer device 10, although other suitable arrangements for securing the cap 52 to the fluid transfer device 10 may be utilized. The gripping surface 56 provides a surface for a user to engage to remove the cap 52 from the fluid transfer device 10 prior to use.

Referring to FIGS. 18-21, a patient connector 62 and packaging 64 for the patient connector 62 is shown in accordance with one aspect of the present invention. The packaging 64 is shown as transparent in FIGS. 18-21, although the packaging 64 may or may not be made from a transparent or semi-transparent material. The packaging 64 has an open first end 66 and a second end 68 with a sidewall 70 extending between the first and second ends 66, 68. The open first end 66 of the packaging 64 is closed by a removable closure (not shown). The packaging 64 includes a plurality of ribs 72 extending radially inward adjacent to the second end 68 of the packaging 64 that are configured to engage the patient connector 62 and restrict movement of the patient connector 62 within the packaging 64. Further, the packaging 64 includes external ribs 73 that extend radially outward from the sidewall 70 of the packaging 64, which may provide additional structural support and/or an additional gripping surface for the packaging 64. The packaging 64 also includes a plurality of guide protrusions 74 positioned adjacent the first end 66 of the packaging 64. The guide protrusions 74 include tapered surfaces 76 that are configured to guide a portion of the patient connector 62 into the packaging 64. In particular, the patient connector 62 includes a plurality of protrusions 78 extending radially outward from the patient connector 62 that are configured to be received between the plurality of guide protrusions 74 of the packaging 64 with the tapered surfaces 76 of the packaging 64 cooperating with tapered surfaces 80 of the plurality of protrusions 78 of the patient connector 62 to guide insertion of the patient connector 62 into the packaging 64. The positioning of the plurality of protrusions 78 between the guide protrusions 74 of the packaging 64 restricts rotational movement of the patient connector 62 relative to the packaging 64 to prevent wear and damage to the packaging 64 and patient connector 62 and also to facilitate connection of the patient connector 62 to a patient line (not shown). In other words, a patient line may be secured to the patient connector 62 while the patent connector 62 is positioned within the packaging 64, which is easier with the patient connector 62 rotationally fixed relative to the packaging 64.

Although the invention has been described in detail for the purpose of illustration based on what is currently considered to be the most practical and preferred aspects, it is to be understood that such detail is solely for that purpose and that the invention is not limited to the disclosed aspects, but, on the contrary, is intended to cover modifications and equivalent arrangements that are within the spirit and scope of the appended claims. For example, it is to be understood that the present invention contemplates that, to the extent possible, one or more features of any aspect can be combined with one or more features of any other aspect.

The invention claimed is:

1. A fluid transfer system comprising:
   packaging comprising:
      a body having a sidewall extending between an open top end and a bottom end and defining an interior cavity; and
      at least one projection extending radially inward from the sidewall into the interior cavity; and
   a fluid transfer device configured to be received within the interior cavity, the fluid transfer device comprising:
      an inner member configured to be secured to a container;
      an outer member surrounding at least a portion of the inner member, the inner member having a first axial position relative to the outer member where the inner member is configured to rotate freely in a first and a second rotational direction relative to the outer member and a second axial position where rotation of the inner member relative to the outer member is restricted in the first rotational direction; and
      a locking arrangement provided on at least a portion of the inner member and accessible through at least a portion of the outer member,
   wherein the locking arrangement is configured for cooperating with the at least one projection to prevent rotation of the inner member relative to the outer member upon an application of a compressive force on the packaging.

2. The fluid transfer system of claim 1, wherein the at least one projection is a pair of projections that are oriented opposite from each other around a circumference of the packaging.

3. The fluid transfer system of claim 1, wherein the packaging further comprises at least one button extending radially outward from an outer portion of the sidewall opposite the at least one projection.

4. The fluid transfer system of claim 3, wherein the at least one projection is configured to deflect radially inward in response to the compressive force directed to the at least one button.

5. The fluid transfer system of claim 1, wherein the outer member of the fluid transfer device defines an opening configured to receive the at least one projection of the packaging when the fluid transfer device is positioned within the interior cavity of the packaging.

6. The fluid transfer system of claim 5, wherein the at least one projection of the packaging and the opening of the outer member of the fluid transfer device cooperate to prevent rotation of the fluid transfer device relative to the packaging when the fluid transfer device is positioned within the interior cavity of the packaging.

7. The fluid transfer system of claim 5, wherein the at least one projection of the packaging is configured to engage the locking arrangement through the opening in the outer member of the fluid transfer device to prevent rotation of the inner member relative to the outer member when the fluid transfer device is positioned within the interior cavity of the packaging.

8. The fluid transfer system of claim 1, wherein the locking arrangement comprises a recess defined by the inner member, the recess having an engagement surface configured to engage the at least one projection of the packaging.

9. The fluid transfer system of claim 1, wherein the inner member comprises a luer connection.

10. The fluid transfer system of claim 1, wherein the inner member and the outer member define a ratchet arrangement, and wherein the ratchet arrangement is only engaged when the inner member is in the second position.

11. The fluid transfer system of claim 1, wherein the packaging defines a plurality of ribs extending radially inward from the sidewall of the packaging, the plurality of ribs configured to engage a portion of the fluid transfer device when the fluid transfer device is positioned within the interior cavity of the packaging.

12. The fluid transfer system of claim 1, further comprising a seal arrangement positioned within the outer member, the seal arrangement is moveable within the outer member and configured to engage a mating connector, the seal arrangement having an actuated position adjacent to the inner member and an initial position spaced from the inner member, wherein the seal arrangement prevents the inner member from moving from the first position to the second position when the seal arrangement is in the actuated position.

13. The fluid transfer system of claim 12, wherein the inner member and the outer member define a ratchet arrangement, wherein the ratchet arrangement is only engaged when the inner member is in the second position.

14. A fluid transfer device comprising:
   an inner member configured to be secured to a container;
   an outer member surrounding at least a portion of the inner member, the inner member having a first axial position relative to the outer member where the inner member is configured to rotate freely in a first and a second rotational direction relative to the outer member and a second axial position where rotation of the inner member relative to the outer member is restricted in the first rotational direction; and
   a seal arrangement positioned within the outer member, the seal arrangement is moveable within the outer member and configured to engage a mating connector, the seal arrangement having an actuated position adjacent to the inner member and an initial position spaced from the inner member, wherein the seal arrangement prevents the inner member from moving from the first position to the second position when the seal arrangement is in the actuated position.

15. The fluid transfer device of claim 14, wherein the inner member and the outer member define a ratchet arrangement, wherein the ratchet arrangement is only engaged when the inner member is in the second position.

16. The fluid transfer device of claim 14, further comprising a locking arrangement provided on at least a portion of the inner member and accessible through at least a portion of the outer member.

17. The fluid transfer device of claim 16, wherein the locking arrangement comprises a recess defined by the inner member, the recess having an engagement surface.

* * * * *